United States Patent [19]

Roberts

[11] Patent Number: 4,756,690

[45] Date of Patent: Jul. 12, 1988

[54] SUPPORT FRAME FOR UPPER DENTURES, AND METHOD

[76] Inventor: Harold D. Roberts, 1914 N. 37th St., Seattle, Wash. 98103

[21] Appl. No.: 938,458

[22] Filed: Dec. 5, 1986

[51] Int. Cl.⁴ .............................................. A61C 8/00
[52] U.S. Cl. ..................................... 433/176; 433/173
[58] Field of Search ........................ 433/172, 173, 176

[56] References Cited

U.S. PATENT DOCUMENTS

| | | | |
|---|---|---|---|
| 3,739,476 | 6/1973 | Roberts | 433/176 |
| 3,889,375 | 6/1975 | Roberts | 433/176 |
| 4,370,134 | 1/1983 | Roberts | 433/173 |
| 4,379,694 | 4/1983 | Riess | 433/173 |

*Primary Examiner*—John J. Wilson
*Attorney, Agent, or Firm*—Eugene M. Eckelman

[57] ABSTRACT

A U-shaped bar is arranged for connection of an artificial denture thereto and includes segments arranged to be implanted in the upper jaw bone and in the zygomatic bone. The bar and implant segments are formed of a sturdy but bendable material capable of shaping at the time of installation. The segments to be implanted in the jaw bone comprise front and rear segments with non-implant areas therebetween to avoid sinus cavities.

10 Claims, 1 Drawing Sheet

U.S. Patent Jul. 12, 1988 4,756,690
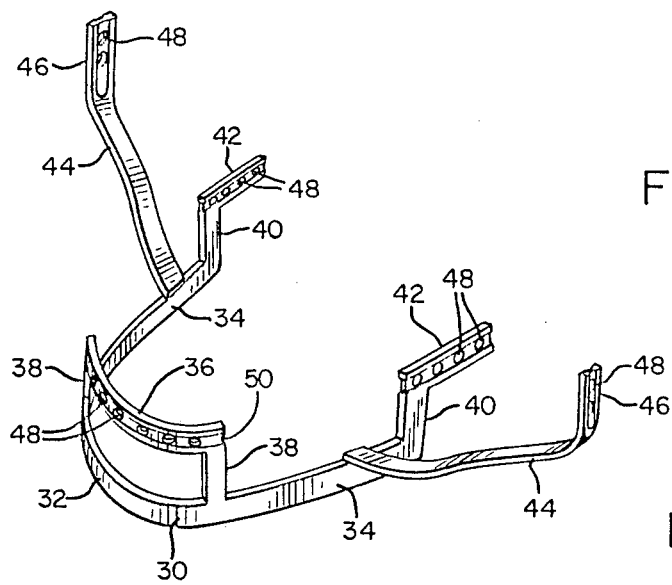
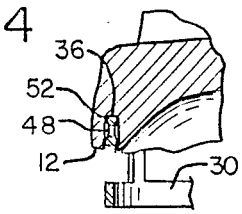
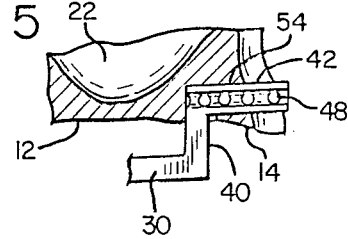
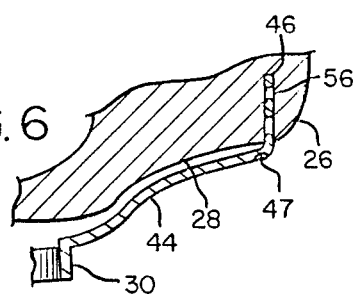
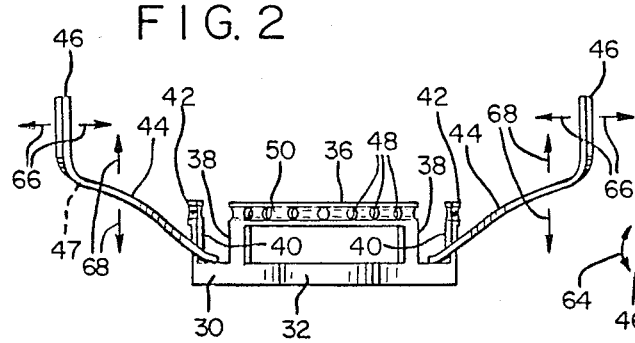
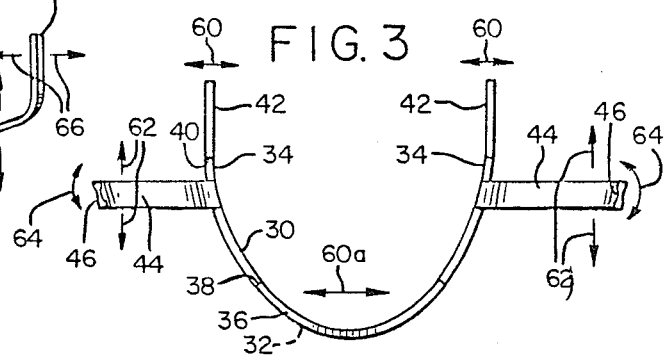
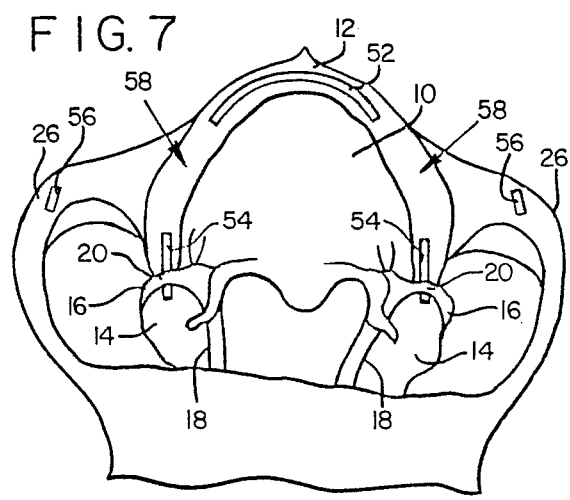
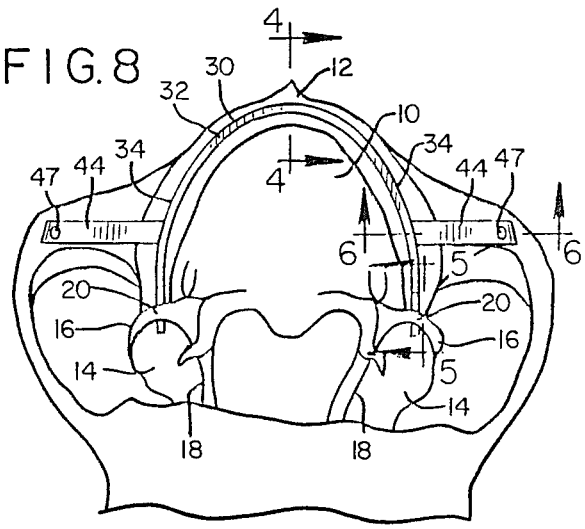

SUPPORT FRAME FOR UPPER DENTURES, AND METHOD

BACKGROUND OF THE INVENTION

This invention relates to new and useful improvements in support frames for upper dentures and more particularly is concerned with implants to be placed and permanently mounted in the upper jaw, and to a method of anchoring such support frame.

Upper jaw implants have heretofore been used for the purpose of providing permanently supported denture means. Some of such prior structures, such as shown in applicant's U.S. Pat. No. 3,889,375, contain a U-shaped body member arranged to be fitted in a recess or channel cut in the alveolar ridge of the upper jaw for receiving an implant rail contoured as necessary. While this structure provides adequate support for implants in most instances even though there is deterioration or damage of the jaw bone, there may not be adequate anchored support in conditions of serious bone deterioration and/or damage. Thus, a problem exists in some cases of providing an anchored support which has little or no deflection and capable of withstanding occlusal forces.

Another problem which exists with relation to upper jaw implants results from the structure of the alveolar ridge that is adjacent to sinus cavities. That is, the bone of this ridge in the area of the cavities is very thin and in many cases cannot receive a recess or groove for an implant. In the event that an implant recess or groove breaks through into communication with a sinus cavity, the implant cannot have good anchored support in this region and furthermore infection is likely.

Still another problem exists with relation to upper jaw implants and that is the discomfort to the patient. If an impression has to be taken, such requires two surgeries and possibly more, one to make the impression and one or more to fit the implant.

SUMMARY OF THE INVENTION

According to the present invention, an improved support frame for upper dentures is provided which has good anchored implant support in the upper jaw, and is particularly useful in upper jaw bones which have serious bone deterioration and/or damage.

Another object of the invention is to provide a support frame of the type described which utilizes implant portions that avoid sinus cavity areas.

Another object of the invention is to provide a support frame of the type described constructed of a semi-rigid material which is capable of securely holding a denture but which is bendable for shaping to a person's mouth and capable of being installed with one sitting of the patient.

A further object of the invention is to provide a support frame of the type described having lateral wing portions with segments capable of being implanted in the zygomatic bones.

Yet a further object is to provide a method of anchoring a support frame in an upper jaw.

In carrying out the above objectives, the invention comprises a U-shaped bar arranged for connection thereto of artificial denture means. The U-shaped bar has upwardly projecting implant means insertable in recesses cut in the alveolar ridge of the upper jaw for securing the bar to the upper jaw. The bar also has lateral wing portions insertable upwardly in recesses cut in the zygomatic bone of a person. In order to avoid sinus cavity areas adjacent to the alveolar ridge, the U-shaped bar has a curved front implant segment and rear implant segments which are spaced from the front segment to provide non-implant areas therebetween in the region of the sinus cavities. The bar and its implant portions are formed of a semi rigid material which can be shaped to the person's mouth. The invention also includes a method of installing a support frame in an upper jaw including the steps of implanting a portion of the bar in recesses cut in the alveolar ridge of the upper jaw and also implanting a portion of the bar in the zygomatic bone.

The invention will be better understood and additional objects and advantages will become apparent from the following description taken in connection with the accompanying drawings.

BRIEF DESCRIPTION OF THE DRAWINGS

FIG. 1 is a perspective view of the support frame of the instant invention;

FIG. 2 is a front elevational view thereof;

FIG. 3 is a top plan view thereof;

FIGS. 4, 5 and 6 are enlarged sectional views taken on the lines 4—4, 5—5 and 6—6 of FIG. 8 respectively;

FIG. 7 is a fragmentary bottom plan view of an upper jaw bone, the zygomatic bones, and other bone associated with the jaw bone, this view showing recesses or openings which have been cut in the jaw bone and zygomatic bone in preparation for installing the present frame; and FIG. 8 is a view similar to FIG. 7 but showing the frame installed.

DETAILED DESCRIPTION OF A PREFERRED EMBODIMENT

With reference first to FIGS. 7 and 8, there is depicted somewhat generally bone structure with which the present implant is associated. FIGS. 7 and 8 are views looking upwardly at the upper jaw or maxilla and also bone structure disposed laterally of the jaw. The numeral 10 represents the palatine bone of the maxilla and the numeral 12 represents the tooth supporting area or the alveolar ridge, also shown in FIGS. 4, 5 and 6. At the posterior or rear of the alveolar ridge of the jaw bone structure and intersecting the longitudinal line of this ridge is the pterygoid bone 14, also shown partially in section in FIG. 5. This latter bone includes buccal and mesial wings 16 and 18, respectively, and this bone has a cortical bridge 20, referred to as the pyramidal process, at the lower anterior portion thereof. This bridge is substantially in the same horizontal plane or a little lower than the lower surface of the alveolar ridge. The reference numeral 22 in FIG. 5 designates a sinus cavity which in most patients of the type having atrophy of the jaw bone is very close to the lower surface of the alveolar ridge 12 and separated only by very thin bone layer.

Laterally of the jaw bone are the zygomatic processes or bones 26, also seen in FIG. 6, the lower surfaces of this bone area tapering upwardly and outwardly with a concaved curvature 28, FIG. 6.

The alveolar ridge 12 has an exterior portion or covering of compact bone and the interior thereof comprises a spongy bone which has a vast amount of blood supply and therefore heals fast. The pterygoid bone, and particularly the pyramidal process thereof, comprises compact bone which provides a good anchoring point for an implant frame portion. The zygomatic bone comprises compact bone similar to the pyramidal process and the alveolar ridge and similarly provides a good anchoring point for an implant frame portion. The present invention was designed to take maximum advantage of compact bone structure for holding an upper support frame securely in implanted relation.

With particular reference to FIGS. 1, 2 and 3, the support frame of the invention comprises a U-shaped bar 30 having a curved front end 32 with substantially straight side extensions 34. Bar 30 comprises the supporting means for the artificial denture or dentures, not shown, which is attached in a conventional manner. A first implant portion comprises a curved segment 36 integral with the bar 30 by means of upright post portions 38. As will be more apparent hereinafter, the curved implant segment 36 is shaped and arranged for fitting in the forward curved portion of the alveolar ridge.

The rearward ends of the bar 30 are turned upwardly in post portions 40, and short rear implant segments 42 lead rearwardly in integral relation from the upper end of these post portions. Implant segments 42 are arranged to be implanted rearwardly in a portion of the alveolar ridge and the pterygoid bone, as will be more apparent hereinafter.

Leading upwardly in integral relation from an upper portion of the bar 30 and intermediate the posts 38 and 40 are wing portions 44. These wing portions angle upwardly and outwardly and have an end segment 46 extending substantially straight upwardly. Small tool engaging recesses or notches 47 are provided in the under surface of the wing portions 44 adjacent the implant segments 46. As will be more apparent hereinafter, the segments 46 are arranged to be implanted in the respective zygomatic bones.

Each of the implant segments 36, 42 and 46 is provided with apertures 48 to receive bone growth for integrated connection of the implant segments into the bone. These segments also have longitudinal side grooves 50 which also receive bone growth.

For the purpose of installing the present support frame, the jaw bone and zygomatic bones are selectively prepared as follows. With reference to FIG. 7, a recess 52 is cut along the lower edge of the alveolar ridge at the front, this recess being selectively made on said ridge in the best area of existing bone and being dimensioned in width and length substantially equal to the front curved implant segment 36. Also, a recess 54 is cut on each side of the alveolar ridge at the rear thereof of a shape and size to fit the implant segments 42. Such grooves may extend under the cortical bridge 20 or through it, depending upon the condition of the bone in this area. Also, a recess 56 is cut on each side in an upwardly direction in the zygomatic bone for receiving the implant segments 46 of the wing portions 44. All of such grooves of course are provided after opening gum and flesh areas for baring the selected portions of the bones.

FIG. 7 illustrates best a concept of the invention wherein a gap 58 is provided between the front recess 52 and the rear recesses 54, the present support frame being designed with such spacing of the front segments 36 from the rear segments 42 to bypass this ridge of bone in the area of sinuses 22.

With particular reference to FIG. 8, and also FIGS. 4, 5 and 6, the support frame is set in place with the implant segments 36, 42 and 46 being received in their respective recesses. These implant segments can be hand set into place with possibly some tapping with a tool, such as tapping on the under side of the frame and tool engagement with the recesses 47. When the bone grows through and around these implant segments, a strong connection is provided that has no undesirable deflection and is capable of standing the normal forces of occlusion. This is particularly so in view of the side mounting of the implant segments 46 in the zygomatic bone.

With particular reference to FIGS. 2 and 3, a feature of the present invention is to form the support frame of a sturdy but semi-rigid material which although being sufficiently strong to adequately support a denture at the same time can be forcefully bent by the dentist so that it can be precisely fitted to a patient in the most efficient manner. With reference first to FIG. 3, the overall U-shape curvature and lateral distance between the side extensions 34 can be varied in both directions as depicted by arrows 60 and 60a. Also, the wing portions 44 can be bent rearwardly or forwardly as depicted by arrows 62. Furthermore, the upright implant segments 46 can be twisted slightly on an upright axis, as depicted by arrows 64 to fit the angle of their respective recesses 56. Also, as seen in FIG. 2, implant segments 46 can be bent relative to the vertical as depicted by arrows 66. Further yet, the wing portions 44 can be bent up and down as depicted by arrows 68 and bent if necessary to underlie and follow the contour 28 of the zygomatic bone comprising a concaved contour. The material to accomplish such shaping comprises a cold-worked or annealed stainless steel capable of being stamped to shape. This avoids the undesirable use of castings which knowingly are brittle.

With the use of material that can be bent for the construction of the support frame, the dentist does not have to take an impression, as would be required by castings, but with the use of an approximately sized support frame it can be contoured by the dentist at the time of installation to fit precisely in the patient in one fitting, as opposed to impression type fittings which require surgery for the impression and a surgery for a later fitting. Also, in avoiding the making of impressions, the over-all costs are low and also no evasive areas of surgery are necessary. Installation of the present implant can generally be accomplished under local anaesthesia. With a minimum number of standard sizes, shaping can be accomplished to fit everyone.

It is to be understood that the form of my invention herein shown and described is to be taken as a preferred example of the same and that various changes in the shape, size and arrangement of parts may be resorted to without departing from the spirit of my invention, or the scope of the subjoined claims.

Having thus described my invention, I claim:

1. A support frame for upper dentures to be fitted to a person comprising:
   a U-shaped bar arranged for connection of artificial denture means thereto,
   upwardly projecting implant means on said U-shaped bar insertable in a recess cut in the alveolar ridge of the upper jaw for securing said bar to the upper jaw,
   and lateral wing portions on said U-shaped bar,
   said lateral wing portions having opposite ends, a first end thereof leading integrally from said bar and the opposite end being angled upwardly for fitting in a recess cut in the zygomatic bone, a portion of said lateral wing portions intermediate said opposite ends having a contour arranged to underlie the zygomatic bone.

2. The support frame of claim 1 wherein said implant means includes a rearward extension arranged to extend at least to the pterygoid bone.

3. The support frame of claim 1 wherein said implant means includes a curved front segment which is similar to the curvature of the alveolar ridge for insertion in a recess cut in the forward portion of the alveolar ridge, and a rearwardly extending shank portion on each side at the rear of said bar, said shank portions being spaced from said front portion to provide non-implant areas therebetween whereby to avoid sinus cavity areas of the person.

4. The support frame of claim 1 wherein said bar and implant means are constructed of semi-rigid material capable of securely holding a denture but bendable for shaping to a person's mouth.

5. The support frame of claim 1 wherein said bar, said implant means, and said lateral wing portions are constructed of semi-rigid material capable of securely holding a denture but bendable for shaping to a person's mouth.

6. The support frame of claim 1 wherein the contour of said lateral wing portions intermediate said opposite ends comprises a concave-convex contour.

7. A method of installing a support frame for an upper denture of a person comprising the steps of:

implanting first upwardly projecting portions of a U-shaped bar in a recess cut in the alveolar ridge of the upper jaw, and implanting at least one second upwardly projecting portion of said U-shaped bar in a recess in the zygomatic bone.

8. The method of claim 7 wherein said first upwardly projecting portions are implanted at the front of the alveolar ridge and at the rear in the area of the pterygoid bone.

9. The method of claim 7 wherein said U-shaped bar is constructed of semi-rigid material and is bent for shaping to a person's mouth at the time of installation.

10. The method of claim 7 wherein said U-shaped bar and said first and second upwardly projecting portions are constructed of semi-rigid material and are bent for shaping to a person's mouth at the time of installation.

* * * * *